US008218803B2

(12) United States Patent
Fickweiler et al.

(10) Patent No.: US 8,218,803 B2
(45) Date of Patent: Jul. 10, 2012

(54) RECEIVER FACILITY WITH AN ELASTICALLY MOUNTED RECEIVER

(75) Inventors: Werner Fickweiler, Bubenreuth (DE); Uli Gommel, Erlangen (DE)

(73) Assignee: Siemens Medical Instruments Pte. Ltd., Singapore (SG)

( * ) Notice: Subject to any disclaimer, the term of this patent is extended or adjusted under 35 U.S.C. 154(b) by 1009 days.

(21) Appl. No.: 12/221,664

(22) Filed: Aug. 5, 2008

(65) Prior Publication Data

US 2009/0041261 A1 Feb. 12, 2009

Related U.S. Application Data

(60) Provisional application No. 60/963,614, filed on Aug. 6, 2007.

(30) Foreign Application Priority Data

Aug. 6, 2007 (DE) ........................ 10 2007 037 024

(51) Int. Cl.
*H04R 25/00* (2006.01)
*H04R 1/10* (2006.01)
*A61B 7/02* (2006.01)

(52) U.S. Cl. .......... 381/322; 381/74; 381/324; 381/325; 381/328; 381/380; 381/382; 181/129; 181/130; 181/135

(58) Field of Classification Search .................... 381/74, 381/322, 325, 328, 380, 324, 382; 181/129, 181/130, 135
See application file for complete search history.

(56) References Cited

U.S. PATENT DOCUMENTS

| | | | | |
|---|---|---|---|---|
| 4,607,720 | A | 8/1986 | Hardt | |
| 4,739,512 | A | 4/1988 | Hartl et al. | |
| 6,129,174 | A * | 10/2000 | Brown et al. | 181/135 |
| 6,253,871 | B1 * | 7/2001 | Aceti | 181/135 |
| 6,310,961 | B1 * | 10/2001 | Oliveira et al. | 381/328 |
| RE38,351 | E | 12/2003 | Iseberg | |
| 6,931,142 | B2 * | 8/2005 | Fushimi | 381/325 |
| 7,372,972 | B2 | 5/2008 | Ach-Kowalewski et al. | |
| 2003/0081805 | A1 * | 5/2003 | Fushimi | 381/325 |
| 2004/0240694 | A1 * | 12/2004 | Wolf | 381/322 |
| 2007/0230731 | A1 * | 10/2007 | Oliveira et al. | 381/328 |
| 2008/0285783 | A1 * | 11/2008 | Gebert et al. | 381/328 |

FOREIGN PATENT DOCUMENTS

| | | | |
|---|---|---|---|
| DE | 8518681 | U1 | 6/1986 |
| DE | 102004009268 | B3 | 10/2005 |
| EP | 0173371 | A1 | 3/1986 |
| WO | 9907182 | A2 | 2/1999 |
| WO | WO 9907182 | A2 * | 2/1999 |
| WO | 0053094 | A1 | 9/2000 |

* cited by examiner

*Primary Examiner* — Zandra V. Smith
*Assistant Examiner* — Jeremy Joy

(57) ABSTRACT

In the case of a receiver facility to be fixed in the auditory canal, particularly for hearing devices with an external receiver, the receiver is to be mounted in the earmold in an acoustically advantageous fashion which guards against contaminations and is also easily exchangeable. Provision is thus made for a receiver facility with a longish receiver and a earmold, which has a borehole, into which the receiver is inserted. A tubular connector, which is more elastic than the receiver and the earmold, is used to accommodate for the most part the longitudinal extension of the receiver in a friction-locking fashion. The connector is for its part force-fitted into a borehole of the earmold in a friction-locking fashion. The receiver is thus elastically mounted and can be easily removed from the earmold together with the connector with the aid of a pin-like tool for replacement purposes.

8 Claims, 4 Drawing Sheets

RECEIVER FACILITY WITH AN ELASTICALLY MOUNTED RECEIVER

CROSS REFERENCE TO RELATED APPLICATIONS

The present application claims the benefit of a provisional patent application filed on Aug. 6, 2007, and assigned application No. 60/963,614. The present application also claims the benefit of a German application No. 10 2007 037 024.7 filed Aug. 6, 2007. Both of the applications are incorporated by reference herein in their entirety.

FIELD OF THE INVENTION

The present invention relates to a receiver facility for a hearing apparatus with a longish receiver and an earmold, which has a borehole, into which the receiver is inserted. The term hearing apparatus is understood here to mean in particular a hearing device, but also any other device for emitting sound which can be worn on the ear, like for instance a headset, earphones and suchlike.

BACKGROUND OF THE INVENTION

Hearing devices are wearable hearing apparatuses which are used to assist the hard-of-hearing. In order to accommodate numerous individual requirements, various types of hearing devices are available such as behind-the-ear (BTE) hearing devices, hearing device with an external receiver (RIC: receiver in the canal) and in-the-ear (ITE) hearing devices, for example also concha hearing devices or completely-in-the-canal (ITE, CIC) hearing devices. The hearing devices listed as examples are worn on the outer ear or in the auditory canal. Bone conduction hearing aids, implantable or vibrotactile hearing aids are also available on the market. The damaged hearing is thus stimulated either mechanically or electrically.

The key components of hearing devices are principally an input converter, an amplifier and an output converter. The input converter is normally a receiving transducer e.g. a microphone and/or an electromagnetic receiver, e.g. an induction coil. The output converter is most frequently realized as an electroacoustic converter e.g. a miniature loudspeaker, or as an electromechanical converter e.g. a bone conduction hearing aid. The amplifier is usually integrated into a signal processing unit. This basic configuration is illustrated in FIG. 1 using the example of a behind-the-ear hearing device. One or a plurality of microphones 2 for recording ambient sound are built into a hearing device housing 1 to be worn behind the ear. A signal processing unit 3 which is also integrated into the hearing device housing 1 processes and amplifies the microphone signals. The output signal for the signal processing unit 3 is transmitted to a loudspeaker or receiver 4, which outputs an acoustic signal. Sound is transmitted through a sound tube, which is affixed in the auditory canal by means of an otoplastic, to the device wearer's eardrum. Power for the hearing device and in particular for the signal processing unit 3 is supplied by means of a battery 5 which is also integrated in the hearing device housing 1.

BTE hearing devices with an external receiver unit (RIC devices) require special attention in respect of the receiver unit. It is thus desirable for the external receiver unit to be able to be fixed into a so-called "Micro Earmold", i.e. a very small model of an earmold.

In order also to meet the requirements in terms of acoustics, the external receiver unit is to be elastically mounted in the earmold. In addition, the external receiver unit should be protected against contaminations as a result of cerumen, sweat etc. The receiver unit should also be exchangeable and it is favorable for the purpose of protecting the receiver if a receiver and/or cerumen protection system can be attached to the receiver unit.

Patent application DE 10 2004 009 268 B3 discloses an ear insert for a hearing system. In accordance with acoustic conditions, a sound exit is molded in an otoplastic. A receiver integrated into the otoplastic can be exchangeably fastened in the otoplastic with the aid of an adapter.

The publication DE 85 18 681 U1 also discloses a hearing aid, the housing of which has a tapering diameter. Parts of the hearing aid are fastened in the otoplastic using a snap-action closure, which has a plurality of appendages resting on the outer periphery of the housing and which act as snap-in stages to which locking edges snap into place when inserting the housing into the otoplastic.

U.S. patent application RE38,351 E also describes a loudspeaker, which can be inserted into an ear with the aid of an elastic earpiece. A housing is inserted into the elastic earpiece, inside of which a receiver is located. The receiver itself is mounted in the housing with a foam material.

SUMMARY OF THE INVENTION

The object of the present invention consists in providing a receiver facility, with which the receiver is mounted in the earmold in a removable, acoustically favorable and sealing manner.

This object is achieved according to the invention by a receiver facility for a hearing apparatus with a longish receiver and an earmold, which has a borehole, into which the receiver is inserted, as well as a tubular connector, with the receiver for the most part being force-fitted with its longitudinal extension into the connector in a friction-locked fashion and the connector for its part being force-fitted into the borehole of the earmold in a friction-locked fashion.

The elastic connector not only ensures a simple exchangeability of the receiver in the earmold but instead also provides for the receiver to be for the most part acoustically decoupled from the earmold. The portion of solid-borne sound which is transmitted from the receiver via the earmold to the auditory canal walls of the user of the hearing apparatus is thus significantly reduced.

A cerumen protection element is preferably force-fitted into the connector at its sound exit side. As a result, the connector not only inheres the function of holding the receiver but also that of holding the cerumen protection system.

The connector can also comprise several ridges extending in a peripheral direction on its outer shell. As a result, very defined pressure and frictional forces can be exerted by the connector on the borehole of the earmold. The forces involved in force-fitting and extruding the connector into/out of the borehole of the earmold can thus be determined in the desired fashion.

The connector can also be manufactured from rubber or a rubbery-elastic plastic. In an elastic connector of this type, the receiver can be easily impressed. Similarly, the connector can then be easily force-fitted into the earmold.

In accordance with a similarly preferred embodiment, the connector seals the receiver in the earmold such that no contamination can enter the sound outlet from the side of the receiver facing the sound outlet of the receiver. As a result, the connector not only inheres a sealing function in respect of the side facing the ear drum, but also in respect of the side is directed outward when in the worn state.

It was already indicated that the above-described receiver facility is preferably used for a BTE hearing device with an external receiver which can be inserted into an auditory canal. A receiver of this type can however also be used for headsets, music playing devices and suchlike.

BRIEF DESCRIPTION OF THE DRAWINGS

The present invention is described in more detail with reference to the appended drawings, in which.

DETAILED DESCRIPTION OF THE INVENTION

The exemplary embodiment illustrated in more detail below represents a preferred embodiment of the present invention.

Figure 1:
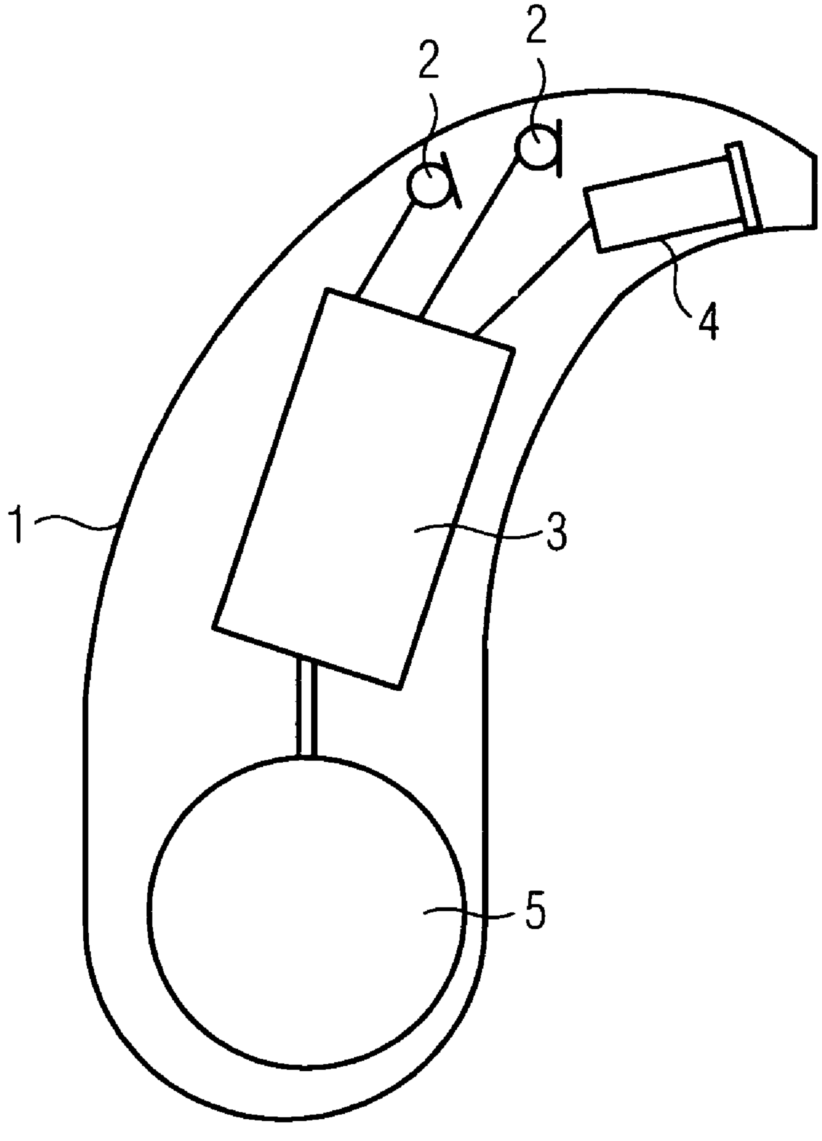
FIG 1 (Prior art)
FIG. 1 shows the basic design of a hearing device according to the prior art.
Figure 2:
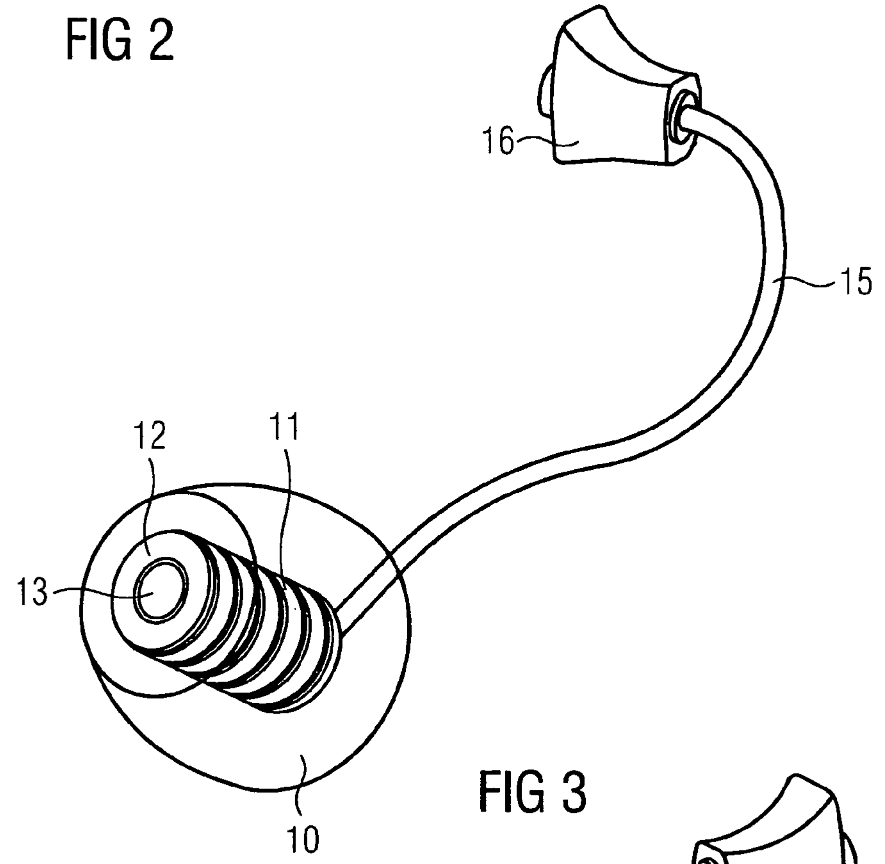
FIG. 2 shows an inventive external receiver facility from the sound exit side.

FIG. 2 shows an external receiver facility for a BTE hearing device, which is itself not shown. The receiver facility is shown from the sound outlet side, i.e. from the side facing the eardrum when the receiver facility is being worn. An earmold 10 can be seen, which approximately takes the form of half an olive. It consists of an elastic material and is able to adjust to the auditory canal of the user. An elastic, cylindrical connector 11, which has its two front faces flush with those of the earmold 10, is located in the earmold 10. The hollow-cylindrical connector 11 is connected to a cerumen protection element 13 on the front face 12 facing toward the eardrum. The cerumen protection element 13 ensures that the receiver 14 located inside the connector 11 (cf. FIG. 3) is not contaminated with cerumen.

Figure 3:
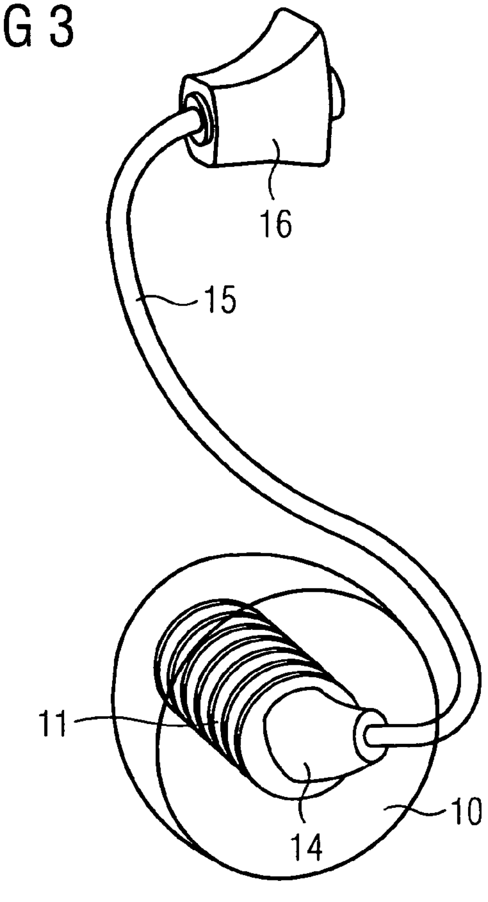
FIG. 3 shows the receiver facility in FIG. 2 from the rear side.

FIG. 3 shows the receiver facility in FIG. 2 from the rear, i.e. from the side which points outwards when being worn. The receiver 14 selected in the example in FIG. 3 protrudes from the connector 12 in the axial direction of the connector 12. However, the earmold 11 but also the connector 11 can also be selected in its axial extension as long as the receiver 14 does not protrude from the connector 12.

FIG. 3 also shows that a cable 15 is guided out of the receiver 14, by way of which cable the receiver is controlled. An adapter 16, which is to be connected to a hearing device so that the corresponding signals can be provided to the receiver 14, is located at the other end of the cable 15.

Figure 4:
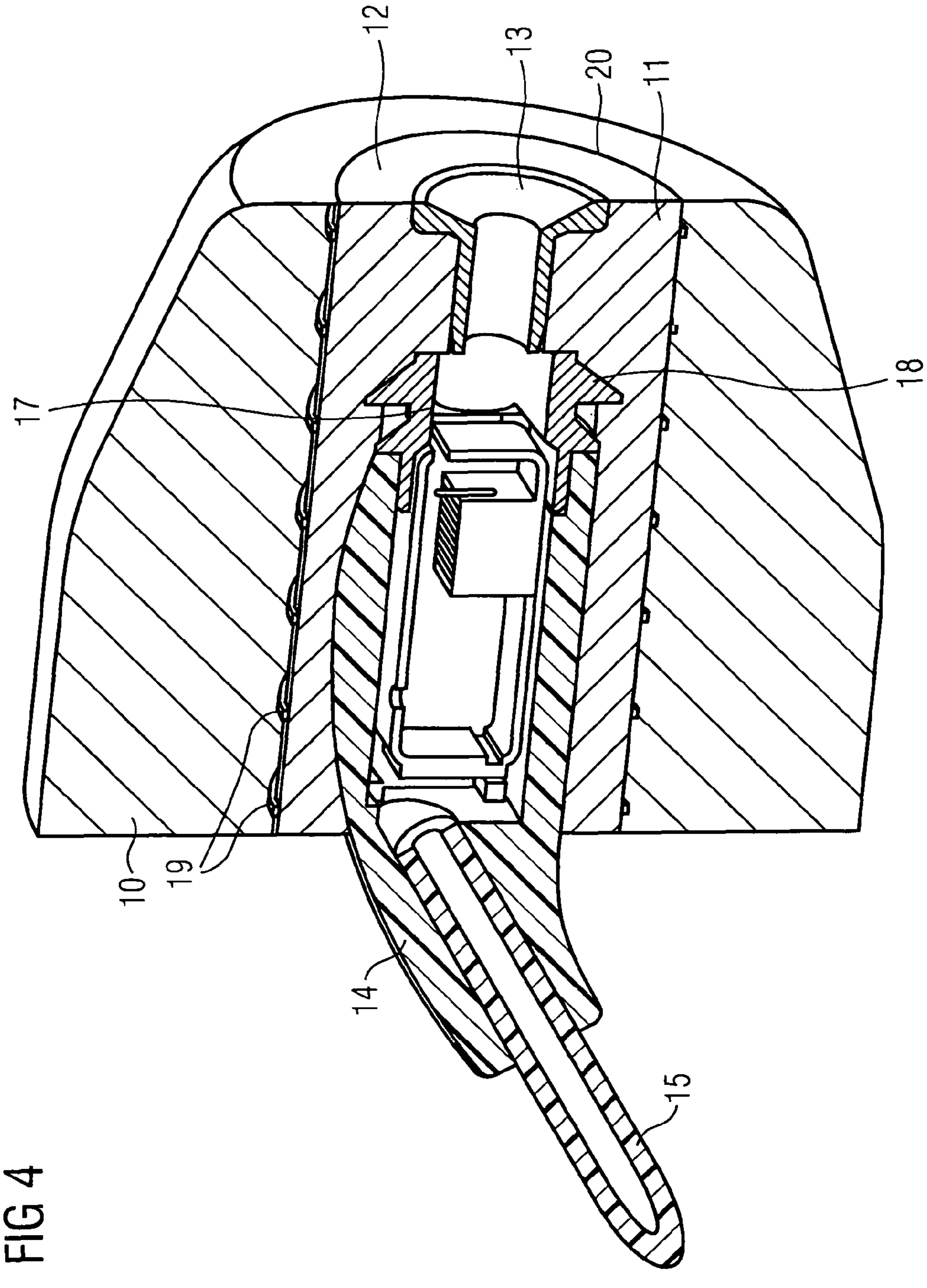
FIG. 4 shows a longitudinal section through the receiver facility in FIG. 2 and FIG. 3

FIG. 4 shows the external receiver facility in FIG. 2 and FIG. 3 including a short piece of the cable 15 and/or its protective shell in the longitudinal section. The outer contour of the housing of the receiver 14 is embedded into the elastic, cylindrical connector 11. To this end, provision can be made in the connector for a correspondingly contoured recess which continues in the axial direction. To improve the hold in the connector 11, the receiver 14 has a sound outlet connecting piece 17 with a circumferential barb 18.

The cylindrical connector 11 has ridges 19 on its outer periphery which extend in the peripheral direction in the example selected. They are made of the same elastic material as the connector 11.

A defined borehole 20, which has approximately the same inner diameter as the connector 11 without the ridges 19, is located in the earmold 10. The unit consisting of receiver 14 and elastic connector 11 is force-fitted into this borehole 20. In this way, the ridges 19 press against the internal circumference of the earmold 10 and are accordingly impressed.

After assembling the unit consisting of receiver 14 and connector 11 into the earmold 10, a cerumen protection system 13 can be force-fitted into the recess of the connector 11 from the front side 12. The cerumen protection system 13 is embodied here to be funnel-shaped and has a membrane on its surface. The funnel of the cerumen protection system 13 is sufficient to reach the sound outlet connecting piece 17 of the receiver 14, so that the sound produced by the receiver 14 is guided outwards through the cerumen protection system 13 and the receiver is simultaneously protected against contaminations by means of the membrane of the cerumen protection system 13. In the event of contamination to the membrane of the cerumen protection system 13, this can be easily removed from the elastic connector 11 and exchanged.

Figure 5:
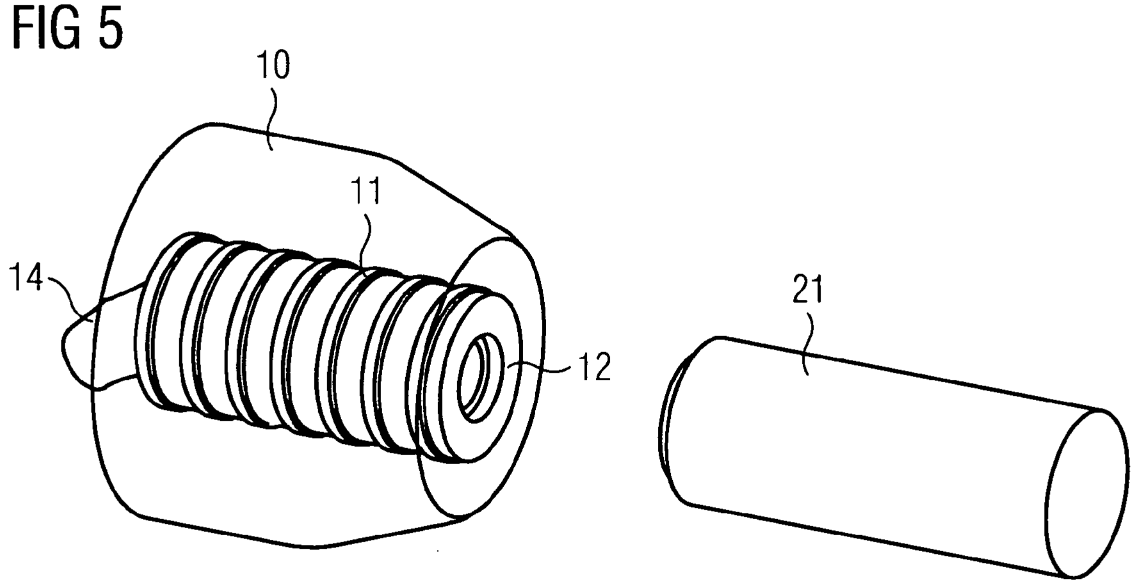
FIG. 5 shows a side view of the receiver facility in FIG. 4 and a dismounting tool.

A tool is preferably used to exchange the receiver 14, which is shown in FIG. 5. On the other hand, there is the risk that the receiver 14 on the cable 15 is pulled out of the earmold 10 and/or connector 11, as a result of which the electrical contacts of the receiver are in some circumstances mechanically overloaded.

The tool 21 shown in FIG. 5 essentially has a cylindrical section, the diameter of which corresponds somewhat to that of the borehole 20 in the earmold 10. The connector 11 can then be pushed out of the earmold 10 using the tool 21, with the pin and/or the tool 21 pressing against the front face 12 of the connector 11 with a front face. The cerumen protection element 13 should in this way already be removed, so that it does not break or become damaged. The receiver 14 itself is also not damaged by extrusion using the tool 21, since it is located inside the connector 11 axially removed from the front face 12.

The receiver facility shown in FIG. 2 to FIG. 5 is advantageous in that it can be replaced quickly and easily. No cerumen, sweat, moisture etc. can thus reach the receiver by mounting the receiver across the complete length of the borehole. The use of an elastic material also allows the receiver to be mounted in an acoustically advantageous fashion. As the elastic connector 11 also seals the receiver 14 on the rear/outer side in the earmold 10, no contamination is able to pass between the earmold 10 and the receiver. In order to clean the external receiver facility, it is thus possible to clean the complete unit, e.g. in an ultrasonic bath. This means that the receiver 14 need not necessarily be removed from the earmold 10.

The invention claimed is:

1. A receiving device for a hearing apparatus, comprising:
- an earmold;
- a borehole arranged in the earmold;
- a connector that is frictionally locked and force-fitted into the borehole such that said connector includes opposing faces which are flush with opposing faces of the earmold;
- a receiver that is longitudinally frictionally locked and force-fitted into a recess of the connector; and
- a tool sized to be positioned within the borehole and configured to press against a front face of the connector to extrude the receiver from the borehole for replacement, wherein a cerumen protection element is force-fitted into a recess of the connector at a sound exit side.

2. The receiving device as claimed in claim 1, wherein the connector comprises a plurality of ridges extending in a peripheral direction on an outer shell of the connector.

3. The receiving device as claimed in claim 1, wherein the connector is manufactured from a rubber or a rubbery-elastic plastic.

4. The receiving device as claimed in claim 1, wherein the connector seals the receiver in the earmold so that no contamination enters a sound outlet of the receiver from a side of the receiver facing the sound outlet.

5. The receiving device as claimed in claim 1, wherein the connector is a tubular connector.

6. A behind-the-ear hearing device, comprising:
   a receiving device comprising:
      an earmold,
      a borehole arranged in the earmold,
      a connector that is frictionally locked and force-fitted into the borehole such that said connector includes opposing faces which are flush with opposing faces of the earmold, and
      a receiver that is longitudinally frictionally locked and force-fitted into the connector; and
   a tool sized to be positioned within the borehole and configured to press against a front face of the connector to extrude the receiver from the borehole for replacement.

7. The behind-the-ear hearing device as claimed in the claim 6, wherein the receiving device is an external receiving device that is inserted into an auditory canal.

8. The receiving device as claimed in claim 1,
   wherein the cerumen protection element is funnel shaped and sized to reach a sound outlet of the receiver within the recess;
   wherein the recess is contoured along an axial direction of the connector;
   and wherein a sound outlet of the receiver within the recess includes a circumferential barb.

* * * * *